(12) United States Patent
Gronovich et al.

(10) Patent No.: US 12,161,364 B2
(45) Date of Patent: Dec. 10, 2024

(54) SURGICAL DEVICE FOR IMPLANT REMOVAL

(71) Applicant: Shaare Zedek Scientific Ltd., Jerusalem (IL)

(72) Inventors: Yoav Gronovich, Maale Hahamisha (IL); Adi Maisel-Lotan, Raanana (IL)

(73) Assignee: Shaare Zedek Scientific Ltd., Jerusalem (IL)

( * ) Notice: Subject to any disclaimer, the term of this patent is extended or adjusted under 35 U.S.C. 154(b) by 687 days.

(21) Appl. No.: 17/290,153

(22) PCT Filed: Oct. 28, 2019

(86) PCT No.: PCT/IL2019/051159
§ 371 (c)(1),
(2) Date: Apr. 29, 2021

(87) PCT Pub. No.: WO2020/089888
PCT Pub. Date: May 7, 2020

(65) Prior Publication Data
US 2021/0401459 A1  Dec. 30, 2021

Related U.S. Application Data

(60) Provisional application No. 62/825,089, filed on Mar. 28, 2019, provisional application No. 62/754,331, filed on Nov. 1, 2018.

(51) Int. Cl.
*A61B 17/34* (2006.01)
*A61F 2/12* (2006.01)

(52) U.S. Cl.
CPC .......... *A61B 17/3468* (2013.01); *A61F 2/12* (2013.01); *A61B 2217/005* (2013.01)

(58) Field of Classification Search
CPC .......... A61B 17/3468; A61B 2217/005; A61B 2017/00561; A61F 2/12; A61M 1/60; A61M 1/602
See application file for complete search history.

(56) References Cited

U.S. PATENT DOCUMENTS 6,558,314 B1    5/2003  Adelman et al.
7,153,294 B1 *  12/2006  Farrow ................. A61M 1/602
                                              604/326

(Continued)

FOREIGN PATENT DOCUMENTS

WO    2018226726 A1    12/2018

OTHER PUBLICATIONS

Bell et al. (2009) Removal of silicone breast implants and review of literature, Canadian Journal of Plastic Surgery, 17(4):e48-e49. Retrieved Jul. 29, 2021 from: https://www.ncbi.nlm.nih.gov/pmc/articles/PMC2827292/pdf/cjps17e48.pdf.

(Continued)

*Primary Examiner* — Ariana Zimbouski
*Assistant Examiner* — Rachel S Highland
(74) *Attorney, Agent, or Firm* — The Roy Gross Law Firm, LLC; Roy Gross (57) ABSTRACT

Device for removal/evacuation of an implant including a collection container with a connector for connection to a suction source and a rimmed opening sized and shaped to enter an implant pocket and to adhere to or juxtapose the implant, such that when suction is applied, the implant is sucked into the collection container.

19 Claims, 4 Drawing Sheets

(56) References Cited

U.S. PATENT DOCUMENTS

| | | | |
|---|---|---|---|
| 2006/0074410 A1 | 4/2006 | Malecki et al. | |
| 2010/0298831 A1* | 11/2010 | Browne | A61B 17/3494 606/79 |
| 2015/0182256 A1 | 7/2015 | Berk et al. | |
| 2016/0066899 A1 | 3/2016 | Lovell | |
| 2018/0193042 A1* | 7/2018 | Wilson | A61B 17/22 |
| 2019/0209290 A1 | 7/2019 | Yousif et al. | |
| 2019/0388118 A1* | 12/2019 | Kirn | A61F 2/12 |
| 2020/0281626 A1* | 9/2020 | Bateman | A61B 17/3468 |

OTHER PUBLICATIONS

Hajdu et al (2010) The barrel-suction method for silicone gel removal from ruptured breast implants, J Plast Reconstr Aesthet Surg., vol. 63, Issue 12, pp. 2197-2198. Retrieved Jul. 29, 2021; doi: 10.1016/j.bjps.2010.05.001.

Naseem et al (2019) Use of bladder syringe to evaluate ruptured breast implants: a neat approach, Annals of the Royal College of Plastic Surgeons of England, vol. 101, Issue 2, pp. 133-134; Retrieved Jul. 29, 2021; doi: 10.1308/rcsann.2018.0110.

Nisi et al (2011) A Simple Atraumatic Way to Remove Breast Implants, Journal of the American Society of Plastic Surgeons, vol. 127, Issue 3, pp. 66e-67e; Retrieved Jul. 29, 2021; doi: 10.1097/PRS.0b013e3182063651.

Hwang et al.(2019) How to do the bottle suction method for removal of a silicone gel breast implant, ANZ Journal of Surgery, 89(6):758-759. Retrieved Jul. 29, 2021 from: https://doi.org/10.1111/ans.15261.

Pizzonia et al.(2019) An Adapted Suction Technique to aid removal of ruptured silicone implants, JPRAS Open, 20, pp. 92-93. Retrieved Jul. 29, 2021 from: https://doi.org/10.1016/j.jpra.2019.04.001.

O'Neill et al.(2006) A novel method to remove silicone gel after breast implant rupture, J Plast Reconstr Aesth Surg. Retrieved Jul. 29, 2021 from: https://www.jprasurg.com/article/S1748-6815(06)00013-1/fulltext.

PCT International Search Report for International Application No. PCT/IL2019/051159, mailed Feb. 20, 2020, 4pp.

PCT Written Opinion for International Application No. PCT/IL2019/051159, mailed Feb. 20, 2020, 6pp.

PCT International Preliminary Report on Patentability for International Application No. PCT/IL2019/051159, issued Apr. 27, 2021, 7pp.

* cited by examiner

SURGICAL DEVICE FOR IMPLANT REMOVAL

CROSS REFERENCE TO RELATED APPLICATIONS

This application is a National Phase of PCT Patent Application No. PCT/IL2019/051159 having International filing date of Oct. 28, 2019, which claims the benefit of priority of U.S. Provisional Patent Application No. 62/754,331, filed Nov. 1, 2018 and U.S. Provisional Patent Application No. 62/825,089, filed Mar. 28, 2018, the contents of which are all incorporated herein by reference in their entirety.

FIELD OF THE INVENTION

The present invention relates generally to the field of devices and a method for removal of implants, specifically to collection containers and methods of using same for evacuating an intact or ruptured breast implant from an implant pocket.

BACKGROUND

Device failure is one of the most common side effects of breast augmentation and reconstruction. Rupture risk increases significantly after 6 years from implantation, with 15% of modern implants expected to rupture between the third- and tenth-year following implantation. Given that breast augmentation is the most common aesthetic plastic surgery procedure (more than 300,000 performed annually in the US alone, meaning 600,000 implants), rupture of breast implants is a very common phenomenon.

Explantation of an implant is typically manually performed. In order to remove the implant, the surgeon pinches the implant with his fingers. Consequently, the implant and its external shell are exposed to forces of compression and traction which greatly increase the possibility of rupturing the prosthesis if not already ruptured. This poses further issues confronting implant manufacturers regarding device warranty. Furthermore, in cases of device failure, ruptured implant removal is very messy and unpleasant. Despite the high frequency of implant rupture and the cumbersome procedure, only a few solutions have been proposed and typically the evacuation is performed manually.

One, at times used, ad hoc solution is utilizing a 60 ml syringe without its plunger, connected to a suction source. The back part of the syringe is then made to adhere to the implant's surface, creating a vacuum system that allows the implant to be removed through traction into the syringe.

However, this solution has numerous disadvantages.
1. The suction is applied to a relatively small part of the implant's surface and therefore has to be intense in order to retract the implant. This may cause further rupture of the implant and/or cause spillage of the implant contents.
2. Due to the small volume of the syringe, only the liquid silicone gel content of the implant is sucked out while the implant shell still requires manual removal.
3. The vast part of breast implants have a volume of several hundred grams. Thus, implant removal requires several syringes and repetition of the procedure. Syringe exchanges may be further associated with lack of sterility, a longer operation, silicone gel spillage during the exchange, higher operative costs and difficulty of ascertaining whether removal of the entire implant has been completed.

Thus, there is a need for a device enabling safe, one-step, clean evacuation of breast implants.

SUMMARY OF THE INVENTION

The present disclosure is directed to the field of safe one-scoop evacuation of implants, in particular to devices and a method for one-scoop evacuation of implants including ruptured implants.

According to some embodiments, there is provided a device, including a collection container comprising a connector configured to allow connection to a suction source and a rimmed opening. During use, at least the part of the container comprising the rimmed opening may be configured to enter the implant pocket through an incision made in the subject's skin, such that the rimmed opening approaches/touches the implant, where after suction is applied, the implant is sucked into the collection container. According to some embodiment, the rim of the opening may include an adhesive capable of adhering the container to the implant.

Advantageously, the herein disclosed device is a sterile, single-use disposable, that enables no-touch removal of the implant, and which requires only a small incision, as compared to manual procedures, to enable its evacuation.

As a further advantage, since the implant is evacuated in its entirety (whether ruptured or not) into the collection container, the volume of the explanted implant can be assessed, and the completion of the removal ascertained. For simplicity of this evaluation, the container may optionally include graduation marks indicative of content volume. Moreover, since the implant is evacuated in its entirety into the collection container, the container with the implant may serve as a packaging means for further transport, e.g. for manufacturer's evaluation.

According to some embodiments, the container may be made of a flexible material enabling it to assume a collapsible, optionally flat configuration, when packaged while being expandable prior to or during use, e.g. being filled with the implant. Alternatively, the container may be made of a semi-rigid or rigid material configured to ensure that the container does not collapse when suction is applied. According to some embodiments, the semi-rigid material may ensure that the container does not collapse when suction is applied, while enabling the container to be squeezed, for example, during maneuvering thereof.

As a non-limiting example, the device may have a form of an elongated collection bag, during use. As another non-limiting example, the container may be dome shaped. According to some embodiments, the container may have various shapes essentially resembling that of the implant being evacuated.

According to some embodiments, there is provided a device for removal/evacuation of an implant from a subject, the device comprising a collection container comprising a connector for connection to a suction source and a rimmed opening sized and shaped to enter the implant pocket and to adhere to or juxtapose the implant, such that when suction is applied, the implant is sucked into the collection container.

According to some embodiments, the rim comprises an adhesive, configured to adhere the collection container to the implant.

According to some embodiments, the rim is sized and shaped to enter the implant pocket and to adhere to or juxtapose the implant from inside the implant pocket.

According to some embodiments, the collection container has a volume of at least 150 cc. According to some embodiments, the collection container has a volume in the range of 200 cc-1000 cc.

According to some embodiments, the connector comprises a valve. According to some embodiments, the valve may be a unidirectional valve. According to some embodiments, the valve may be configured to control the suction force and/or suction intensity applied on the implant.

According to some embodiments, the collection container comprises graduation marks indicative of content volume.

According to some embodiments, the collection container is made of a semi-rigid or rigid material configured to prevent collapse of the collection container when suction is applied. According to some embodiments, the collection container may be made of a material selected from the group comprising Polycarbonate, Polyethelene, polyolefin PVC, DEHP, EVA or any combination thereof.

According to some embodiments, the collection container comprises a skeleton, or other reinforcement element configured to prevent collapse of the container upon application of vacuum. According to some embodiments, the skeleton may be internal to or embedded within the wall of the collection container. According to some embodiments, the skeleton may be coextensive with the wall of the container. According to some embodiments, the skeleton may be made of a plurality of enforcing strips. According to some embodiments, the skeleton may be made from or include a polymeric material such as, but not limited to, polyurethane. According to some embodiments, the skeleton may be a braid or a coil made of metal wires, such as, but not limited to, Nickel titanium wires or stainless steel wires.

According to some embodiments, the collection container has a first folded/collapsed configuration and a second unfolded/expanded configuration. According to some embodiments, the collection container is configured to assume its unfolded/expanded configuration prior to use.

According to some embodiments, the implant is a breast implant. According to some embodiments, the implant is a gluteal implant. According to some embodiments, the implant is a ruptured implant. According to some embodiments, the implant is a silicone implant.

According to some embodiments, prior to use, the adhesive on the rim is covered by a removable cover.

According to some embodiments, the device further comprises a cover configured to close off the opening.

According to some embodiments, there is provided a method for removing an implant from a subject, the method comprising: providing a collection container comprising a connector for connection to a suction source and a rimmed opening; inserting at least the rimmed opening into the implant pocket; adhering/juxtaposing the opening to the implant; and applying suction, thereby sucking the implant into the collection container.

According to some embodiments, the implant is a ruptured implant. According to some embodiments, the implant is a silicone implant. According to some embodiments, the implant is a breast implant. According to some embodiments, the implant is a gluteal implant.

According to some embodiments, the method further comprises making the incision at the port of entry in the subject's skin (i.e. allowing access to the implant pocket).

According to some embodiments, the rim comprises an adhesive, configured to adhere the collection container to the implant. According to some embodiments, the rim is sized and shaped to enter the implant pocket.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided a device for removal of an implant, such as, but not limited to, a breast implant, or a gluteal implant from a subject, the device comprising a collection container comprising a connector at one end thereof for connection to a suction source and a rimmed opening at another, optionally opposite end thereof.

According to some embodiments, the rim of the opening comprises an adhesive. According to some embodiments, the adhesive is a surgical drape adhesive.

According to some embodiments, the collection container may include a neck/channel terminating with the rimmed opening.

According to some embodiments, the neck/channel may be configured for insertion into an implant pocket through an incision made in subject's skin. According to some embodiments, the neck/channel of the collection container may have a smaller diameter than the remainder of the container or to parts of the container proximal to the neck/channel. According to some embodiments, the diameter or major axis of the neck/channel may be less than 6 cm, less than 5 cm or less than 4 cm. Each possibility is a separate embodiment.

According to some embodiments, the neck/channel includes a weakened area enabling manual tearing or breaking off of the neck/channel in a shape of a funnel. Advantageously, such weakened area allows easy access to the evacuated implant, for example, if it needs to be removed for pathological or manufacturer evaluation.

According to some embodiments, the weakened area may be circumferential, i.e. formed around at least most of the neck, such as around at least 80% of the neck, around at least 85% of the neck, around at least 90% of the neck, around at least 95% of the neck or around at least 90% of circumference of the neck, thus allowing complete or partial detachment of the neck from the remainder of the collection container. According to some embodiments, the weakened area may be formed around the entire circumference of the neck, thus enabling complete removal of the neck portion from the remainder of the container.

According to some embodiments, the weakened area may be at a proximal end of the neck (i.e. the part of the neck opposite the rimmed opening and adjacent to a part of the container having a larger diameter/major axis). Alternatively, the entire neck may be made from a weaker and/or breakable and/or tearable material than the remainder of the container, allowing manual detachment of the neck from the container.

According to some embodiments, the weakening may be obtained by perforation (i.e. punching and tear-off perforation). According to some embodiments, the perforations and/or tear holes may be laser perforation/tear holes. According to some embodiments, the perforations may have a diameter/major axis of less than 1 mm, less than 0.5 mm, less than 0.1 mm or less than 0.05 mm. Each possibility is a separate embodiment. According to some embodiments, the weakening may be obtained by a thinning of the material, making the area prone to breaks. According to some embodiments, the weakening may be obtained by incorporating a material, making the area prone to breaks.

According to some embodiments, the container may be any container configured to receive an evacuated implant.

According to some embodiments, the container may be made of a flexible material, such as, but not limited to, polyolefin PVC, DEHP, EVA or any combination thereof, enabling it to assume a first collapsed configuration allowing efficient packaging and storage, and a second expanded configuration enabling the evacuated implant to be contained therein in its entirety. According to some embodiments, the collection container may assume its unfolded configuration during filling and/or as a result of filling. According to some embodiments, the user may unfold the collection container prior to use.

According to some embodiments, the container may be made of a semi-rigid or rigid material, such as, but not limited to, polycarbonate, polyethelene, silicone, PVC configured to ensure that the container does not collapse when suction is applied. According to some embodiments, the semi-rigid material may enable squeezing of the container, for example, during maneuvering thereof. According to some embodiments, the container may include an inner liner configured to prevent the walls of the container from sticking to each other, when suction is applied. According to some embodiments, the inner liner may be made of or include polytetrafluoroethylene (PTFE) or ultra-high-molecular-weight polyethylene (UHMWPE). According to some embodiments, the inner liner may be made of or include any material configured to reduce the static coefficient of friction, preferably equal to or below 0.4, equal to or below 0.3, equal to or below 0.2 or equal to or below 0.1. Each possibility is a separate embodiment.

According to some embodiments, the container may be an optionally elongated shaped, collection bag. According to some embodiments, the container may be essentially dome-shaped. According to some embodiments, the container may have a shape essentially customized to the size and/or shape of the implant. According to some embodiments, at least part of the container may be transparent. According to some embodiments, the entire container may be transparent.

According to some embodiments, the rim of the collection container is configured to adhere to the subject's skin, such that the opening of the collection container seals around an incision made in the subject's skin and such that, when suction is applied to the first end of the collection bag, the implant is sucked into said collection bag in its entirety.

According to some embodiments, the rim of the collection container is configured to adhere to the implant, such that the opening of the collection container when inserted into the implant pocket through an incision made in the subject's skin adheres to the implant by way of an adhesive or due to suction being applied, thereby causing the implant to be sucked into the collection container in its entirety.

According to some embodiments, the rim of the opening may be made of a same material as the container. According to some embodiments, the rim may be made of a softer and/or more flexible and/or elastic material than the remainder of the container. According to some embodiments, the rim may be made of rubber, silicon, silicone rubber (polysiloxane) or any other suitable soft and/or flexible and/or elastic material. Each possibility is a separate embodiment.

According to some embodiments, the length, diameter and/or major axis of the opening is 5 cm or less, 4 cm or less, or 3 cm or less. Each possibility is a separate embodiment. According to some embodiments, the length, diameter and/or major axis of the opening is in the range of 2-6 cm, or 3-5 cm. Each possibility is a separate embodiment.

According to some embodiments, the rim may be covered by a removable cover configured to be removed prior to use.

According to some embodiments, the collection container has a volume of at least 100 cc, such as 150 cc, 200 cc, 250 cc, 300 cc, 400 cc, 500 cc, 600 cc or any other suitable volume within the range of 100 cc-1000 cc or 200 cc-900 cc or 300 cc-600 cc. Each possibility is a separate embodiment.

According to some embodiments, the connector comprises a valve, mesh or filter configured to prevent content from flowing out through the connector and/or to seal off the connector upon detachment from the suction source. According to some embodiments, the valve may be a one-way valve. According to some embodiments, the valve may be configured to control the suction force and/or suction intensity.

According to some embodiments, the collection container comprises graduation marks indicative of content volume. According to some embodiments, the graduation marks may be printed on a surface of the collection container. Advantageously, the graduation marks may enable determining/evaluating the progress of the implant removal and/or its completion.

According to some embodiments, there is provided a method for removing/evacuating an implant from a subject, the method comprising: providing a collection container comprising a connector for connection to a suction source and a rimmed opening. According to some embodiments, the rim of the opening comprises an adhesive; configured for adhering of the rimmed opening to the subject's skin or to the implant.

According to some embodiments, the rim may be sized and shaped to be inserted into the implant pocket. As a non-limiting example, the part of the collection container comprising the opening may include a channel shaped neck configured to be inserted into the implant pocket, optionally while the remainder of the container remains outside the implant pocket. According to some embodiments, the rim may be sized and shaped to fit/grasp the opening of the implant pocket.

According to some embodiments, the rim may be made of a plastic like material, such as, but not limited to, polycarbonate, Polyethelene, silicone, PVC or the like.

According to some embodiments, the opening of the collection container is configured to seal around an incision made in the subject's skin; such that when suction is applied, the implant is sucked into the collection container. According to some embodiments, the opening of the collection container is configured to adhere to the implant; such that when suction is applied, the implant is sucked into the collection container. According to some embodiments, the at least neck/rimmed opening of the container is configured to be inserted into the implant pocket and/or into the implant itself.

According to some embodiments, the implant may be a breast implant. According to some embodiments, the implant is a gluteal implant. According to some embodiments, the implant may be a ruptured implant. According to some embodiments, the implant may be a silicone implant.

According to some embodiments, the method further comprises making the incision at the port of entry in the subject's skin (i.e. allowing access to the implant pocket, prior to adhering the collection container).

According to some embodiments, the method further comprises detaching the collection container from the subject's skin once removal of the implant is completed.

According to some embodiments, the device may include a cover, cap, lid, plug, string or other means configured to close off the rimmed opening after evacuation of the implant into the container. According to some embodiments, the cover, cap, lid and/or plug may be attached to the device when not in use. According to some embodiments, the cover, cap, lid and/or plug may be detached from the device when not in use. According to some embodiments, the device may further include a cover, cap, lid or other means configured to seal off the connector upon detachment from the suction source. Alternatively, or additionally, the connector may include a one-way valve configured to seal off the connector upon detachment from the suction source. It is understood that by sealing off the container's openings, the container may serve as a shipping emballage for the removed implant.

Figure 1:
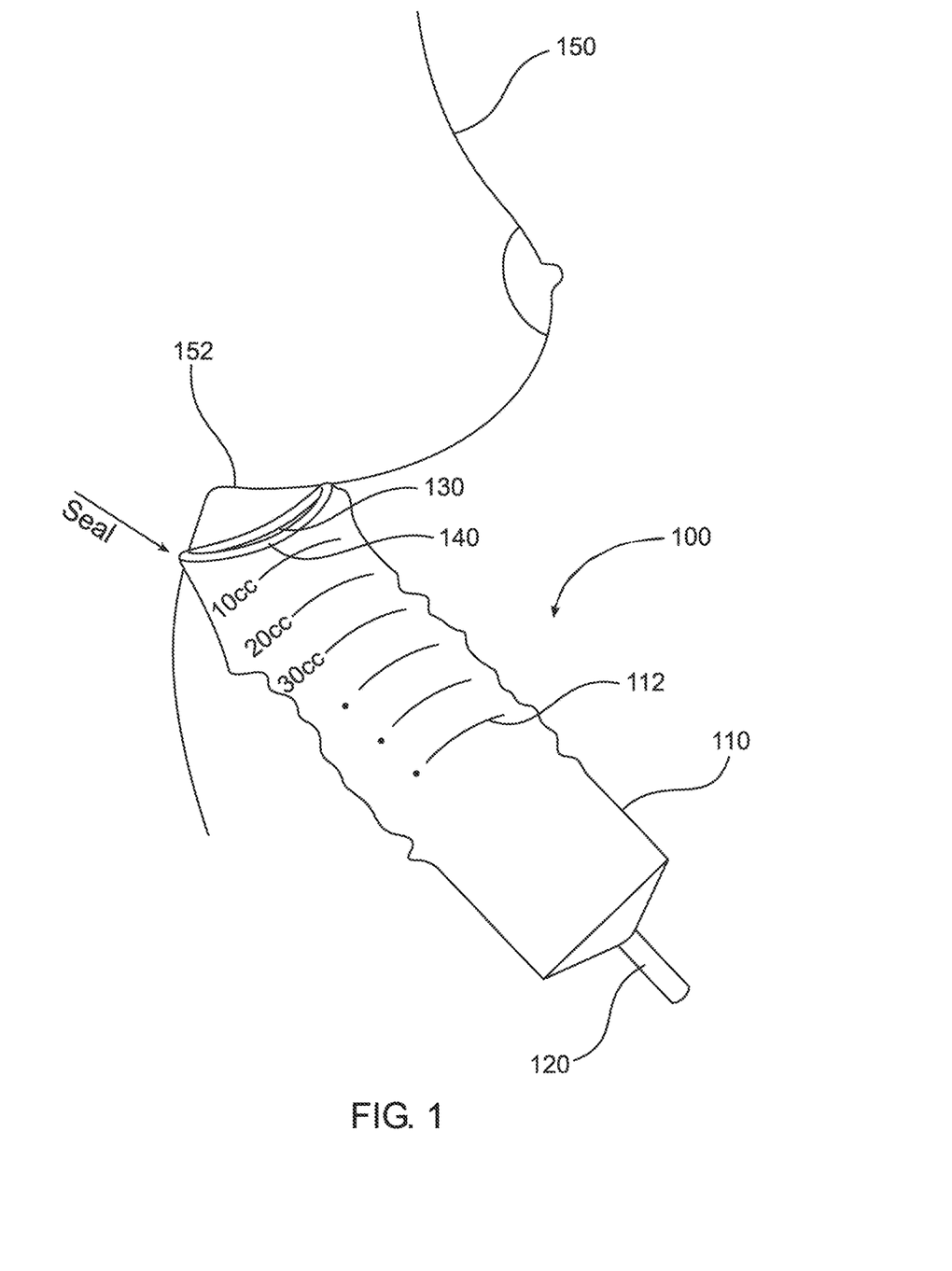
FIG. 1 schematically illustrates a device for implant removal, according to some embodiments.
Figure 2A:
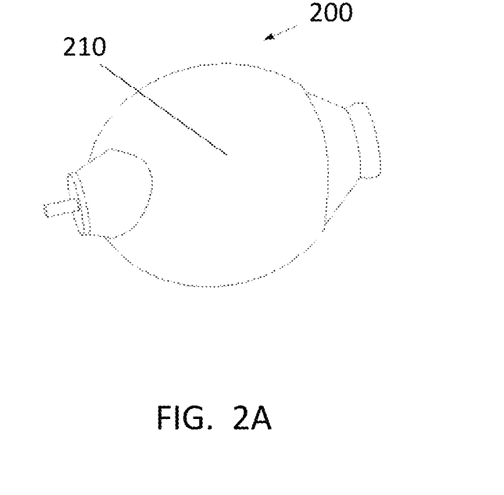
FIG. 2A-2D show perspective, side, front and top views, respectively of a device for implant removal, according to some embodiments.
Figure 2B:
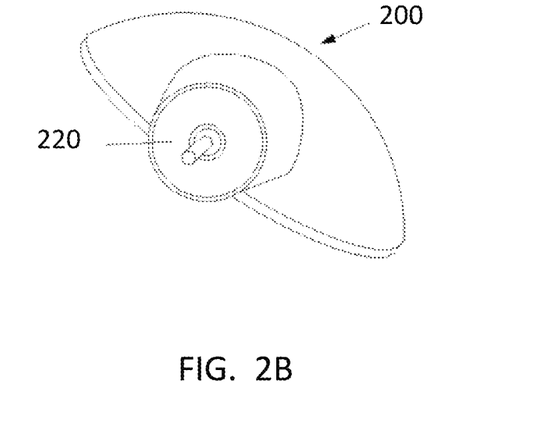
Figure 2C:
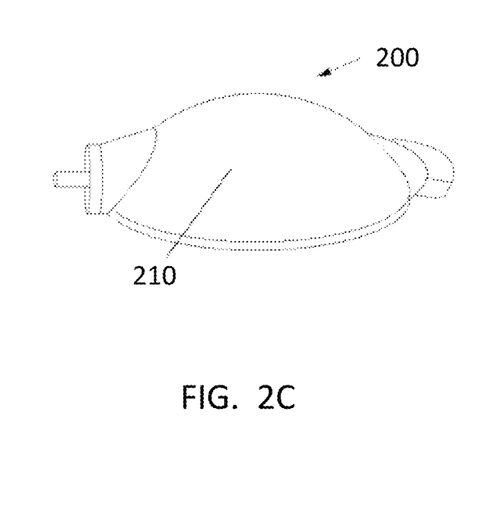
Figure 2D:
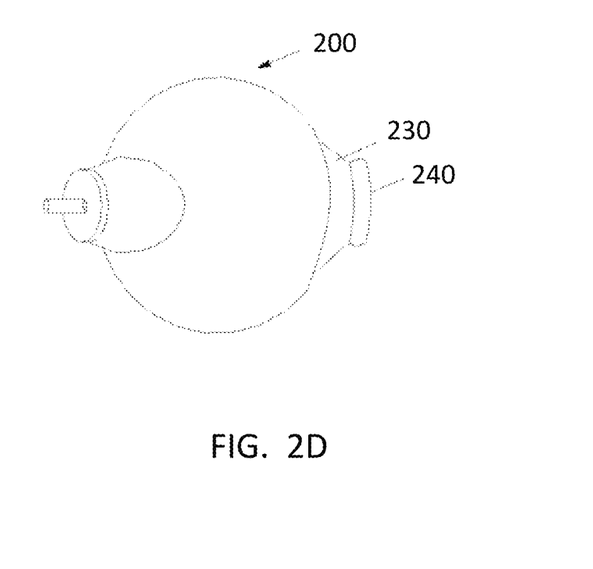

Reference is now made to FIG. 1, which schematically illustrates a device 100 for implant removal, according to some embodiments. Implant removal device 100 includes a collection bag 110 having a first end including a connector 120 for connection to a suction source (not shown) and a second end having an opening 130 at least partially surrounded by a rim 140. Rim 140 includes an adhesive configured to adhere to the subject's skin such that opening 130 of collection bag 110 seals around an incision 152 made in the subject's skin, here the subject's breast 150. Once sealed around incision 152, suction can be applied to the first end of collection bag 110, thereby causing the implant (not shown) to be sucked into collection bag 110 essentially in its entirety. According to some embodiments, rim 140 may be covered by a removable cover (not shown) covering the adhesive, which cover may be removed prior to use.

Collection bag 110 is preferably made of a flexible material enabling it to assume a first collapsed configuration allowing efficient packaging and storage, and a second expanded configuration enabling the evacuated implant to be contained therein in its entirety. According to some embodiments, collection bag 110 may assume its unfolded configuration during filling and/or as a result of filling.

Optionally, collection bag 110 may include graduation marks, such as graduation marks 112, indicative of the volume of the content in collection bag 110. Advantageously, the graduation marks 112 may enable determining/evaluating the progress of the implant removal and/or its completion.

Reference is now made to FIG. 2A-2D, which show illustrative images of an implant removal device 200, (perspective, side, top and front views) according to some embodiment. Implant removal device 200 includes a collection container 210 including a connector 220 for connection to a suction source (not shown) and a neck formed opening 230. The rim 240 of opening 230 may optionally include an adhesive configured to adhere to an implant, such that opening 230 of collection container 210 seals around a portion the implant.

Once opening 230 is juxtaposed to implant (with or without adhering by adhesive), suction can be applied through connector 220, thereby causing the implant to be gradually sucked into collection container 210 essentially in its entirety.

Collection container 210 is preferably made of a semi-rigid or rigid material enabling it to maintain its shape (prevent collapse), when suction is applied and thus to receive the evacuated implant in its entirety.

According to some embodiments, implant removal device 200 may include a cover configured to close off opening 230, for example, after evacuation of the implant therein. This may advantageously allow implant removal device 200 to serve as a packaging means for further transport, e.g. for manufacturer's evaluation of the implant.

Figure 3:
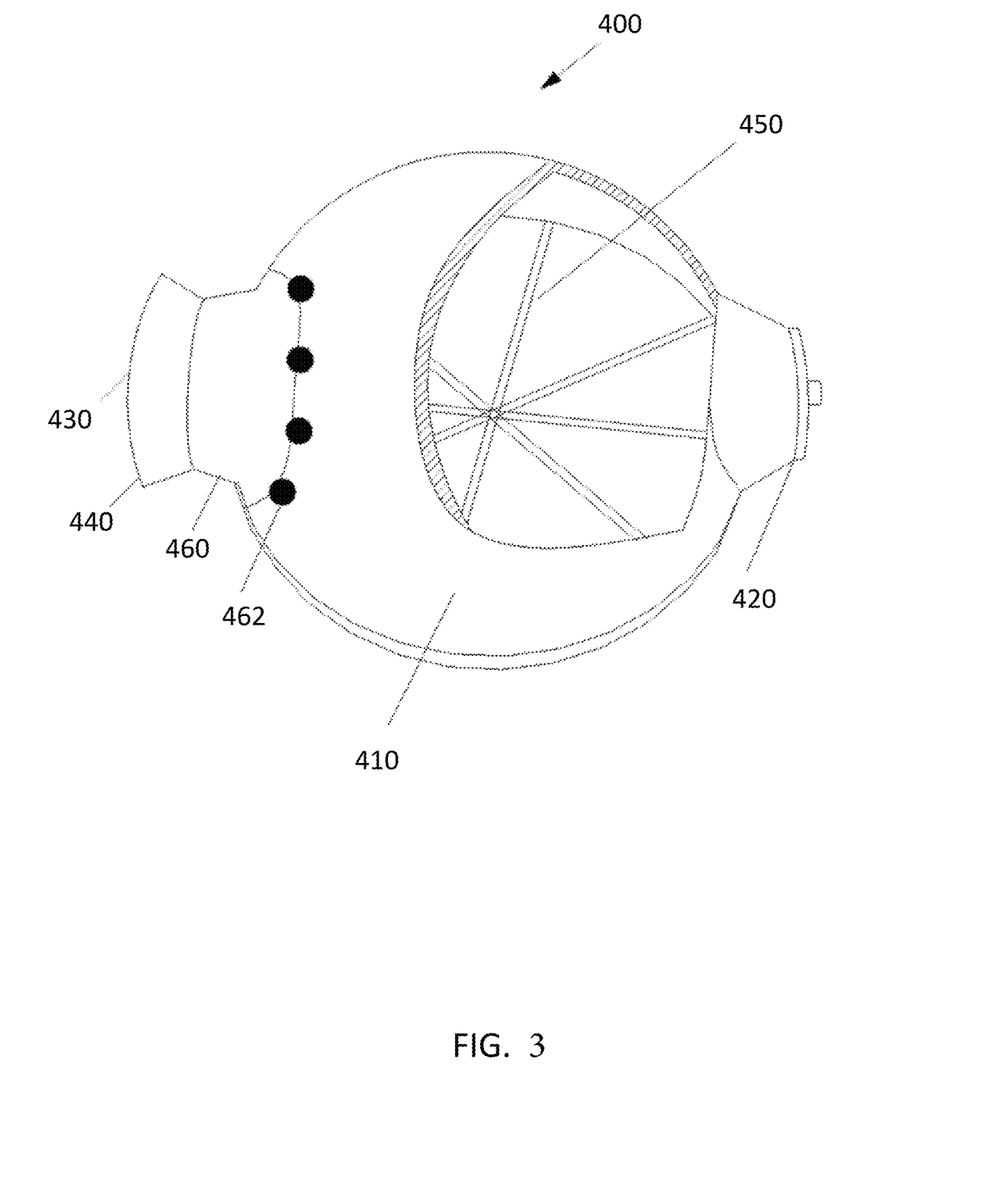
FIG. 3 schematically illustrates a device for implant removal, according to some embodiments.

Reference is now made to FIG. 3, which schematically illustrates a device 400 for implant removal, according to some embodiments. Implant removal device 400 includes a collection container 410 including a connector 420 for connection to a suction source (not shown) and a second end having an opening 430 at least partially surrounded by a rim 440. Rim 440 may optionally include an adhesive configured to adhere to the subject's skin such that rim 440 of collection container 410 becomes attached to the implant (not shown) upon insertion into the incision pocket made in the subject's skin (not shown) and juxtaposition to the implant.

Optionally, collection container 410 may include graduation marks (not shown), indicative of the volume of the content in collection container 410. Advantageously, the graduation marks may enable determining/evaluating the progress of the implant removal and/or its completion.

Collection container 410 includes a skeleton 450 configured to prevent collapse of the container upon application of suction. Skeleton 450 may be internal to or, as here shown, embedded within the wall of collection container 410.

The part of the container, including opening 430, may have a shape of a neck, channel or similar configuration reducing its diameter or major axis, such as neck 460 and thereby easing the insertion of the neck into the implant pocket. The diameter or major axis of neck 460 is preferably less than 6 cm, less than 5 cm or less than 4 cm. Neck 460 optionally includes a weakened area enabling manual tearing or breaking off of neck 460. Advantageously, such tearing off of neck 460 allows easy access to the evacuated implant, for example, if it needs to be removed for pathological or manufacturer evaluation. The weakened area may, as here shown, be formed by punch perforations 462. However other means of forming a weakened area, such as a thinning of the material or incorporation of a weaker material can also be envisaged and, as such, fall within the scope of this disclosure. Punch perforations 462 are here, for illustrative purposes, shown as being relatively large. However, it is understood from one of ordinary skill in the art that the size of perforations 462 is configured to ensure that the content of container 410 (e.g. the fill of the implant) does not flow out of container 410. According to some embodiments, punch perforations 462 may have a diameter/major axis of less than 1 mm, less than 0.5 mm, less than 0.1 mm or less than 0.05 mm. The weakened area may be circumferential, i.e. formed around at least most of neck 460, such as around at least 80% of neck 460, around at least 85% of neck 460, around at least 90% of neck 460, around at least 95% of neck 460, around at least 90% of neck 460, or around the entire circumference of neck 460, thus allowing complete or partial detachment of neck 460 from the remainder of collection container 410. According to some embodiments, the weakened area may be at a proximal end of neck 460. Alternatively, the entire neck may be made from a weaker and/or breakable and/or tearable material than the remainder of the container allowing manual detachment of the neck from the container.

Figure 4:
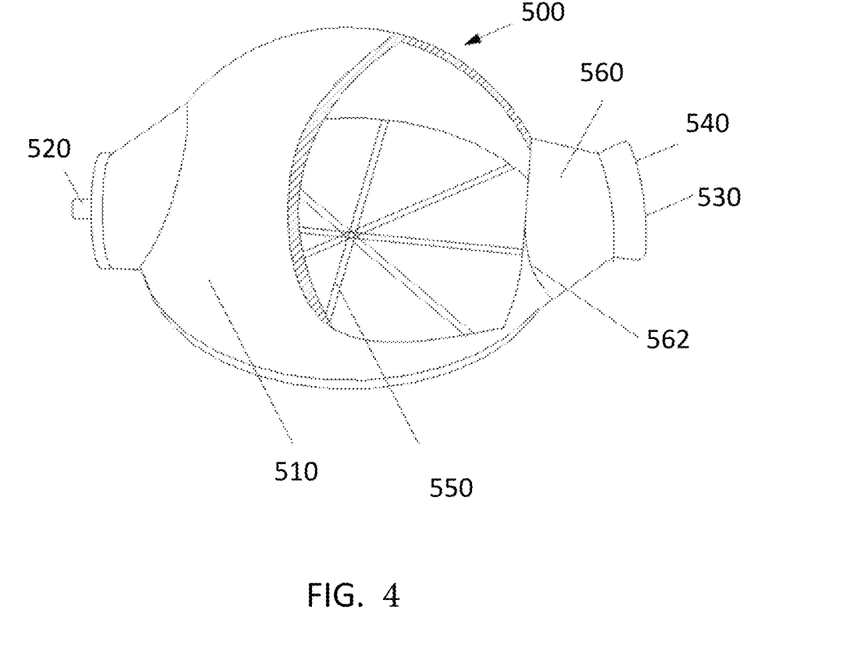
FIG. 4 schematically illustrates a device for implant removal, according to some embodiments.

Reference is now made to FIG. 4, which schematically illustrates a device 500 for implant removal, according to some embodiments. Implant removal device 500 includes a collection container 510 including a connector 520 for connection to a suction source (not shown) and a second end forming a neck 560 terminating with an opening 530. Neck 560 (or channel or other configuration configured to reduce the diameter or major axis of the collection container) is configured for insertion into the implant pocket. Opening 560 is surrounded by a rim 540, which optionally includes an adhesive configured to adhere to the implant.

The diameter or major axis of neck 560 is preferably less than 6 cm, less than 5 cm or less than 4 cm. Neck 560 may optionally include a weakened area 562 enabling manual tearing or breaking off of neck 560. Advantageously, such tearing off of neck 560 allows easy access to the evacuated implant, for example, if it needs to be removed for pathological or manufacturer evaluation. Weakened area 562 may be formed by punch perforations, thinning of the material, or incorporation of a weaker material or other disconnection means. Weakened area 562 may be circumferential, i.e. formed around at least most of neck 560, such as around at least 80% of neck 560, around at least 85% of neck 560, around at least 90% of neck 560, around at least 95% of neck 560, around at least 98% of neck 560, or around the entire circumference of neck 560, thus allowing complete or partial detachment of neck 560 from the remainder of collection container 510. According to some embodiments, weakened area 562 may be at a proximal end of neck 560. Alternatively, the entire neck may be made from a weaker and/or breakable and/or tearable material than the remainder of the container allowing manual detachment of the neck from the container.

Optionally, collection container 510 may include graduation marks (not shown), indicative of the volume of the content in collection container 510. Advantageously, the graduation marks may enable determining/evaluating the progress of the implant removal and/or its completion.

Collection container 510 includes a skeleton 550 configured to prevent collapse of the container upon application of suction. Skeleton 550 may be internal to or, as here shown, embedded within the wall of collection container 510.

According to some embodiments, collection container 510 may be made of polycarbonate. According to some embodiments, skeleton 550 may be made of metal wires, such as, but not limited to, stainless steel wires.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A device for removal or evacuation of an implant from a subject, the device comprising a collection container having a flat lower surface and a dome-shaped top surface, the collection container comprising: a connector for connection to a suction source, an oval-shaped rimmed opening sized and shaped to enter the implant pocket and to adhere to or juxtapose the implant, such that when suction is applied, the implant is sucked into said collection container, and a skeleton comprising a plurality of enforcing strips, the skeleton configured to resist collapse of the collection container, when suction is applied, wherein the skeleton is internal to or embedded within a wall of the collection container; wherein the device comprises an hourglass-like shaped neck comprising the rimmed opening.

2. The device according to claim 1, wherein the rimmed opening comprises an adhesive, configured to adhere the collection container to the implant.

3. The device according to claim 1, wherein the rimmed opening has a diameter or major axis in the range of 2-5 cm.

4. The device according to claim 1, wherein the collection container has a volume in the range of 200-900 cc.

5. The device according to claim 1, wherein the connector comprises a one-way valve.

6. The device according to claim 1, wherein the collection container comprises graduation marks indicative of content volume.

7. The device according to claim 1, wherein the collection container is made of a semi-rigid material configured to prevent collapse of the collection container when suction is applied.

8. The device according to claim 1, wherein the collection container is made of a material selected from the group comprising polycarbonate, polyethelene, polyolefin PVC, DEHP, EVA or any combination thereof.

9. The device according to claim 1, wherein the collection container has walls, and wherein an inner surface of each wall is coated with an inner liner configured to reduce friction between the inner surfaces of the walls, wherein the inner liner comprises polytetrafluoroethylene, and wherein the inner liner has a static coefficient of friction of below 0.3.

10. The device according to claim 1, wherein a narrow aspect of the hourglass-like shape of the neck has a diameter or major axis in a range of 2 cm-4 cm.

11. The device of claim 1, wherein the neck comprises a weakened area configured to enable manual tearing or breaking off of the neck.

12. The device according to claim 1, further comprising a cover, cap, lid, or plug configured to close off the opening after evacuation of the implant.

13. The device according to claim 12, further comprising a second cover, cap, or lid configured to close off the connector after disconnection from the suction source.

14. The device according to claim 1, wherein a distal end of the rimmed opening is flat.

15. The device according to claim 1, wherein the neck has a length of 2-6 cm.

16. The device according to claim 1, wherein the skeleton is made from a polymeric material.

17. The device according to claim 1, wherein the skeleton is made from braided or coiled metal wires.

18. The device according to claim 1, wherein the skeleton is star shaped.

19. The device according to claim 1, wherein the skeleton is positioned on or in the lower surface of the container.

* * * * *